(12) United States Patent
Johansson

(10) Patent No.: US 7,701,575 B2
(45) Date of Patent: Apr. 20, 2010

(54) FIBER QUALITY TRANSDUCER

(76) Inventor: Ola M. Johansson, 2490 Whipple Tree La., Brookfield, WI (US) 53045

(*) Notice: Subject to any disclaimer, the term of this patent is extended or adjusted under 35 U.S.C. 154(b) by 498 days.

(21) Appl. No.: 11/697,813

(22) Filed: Apr. 9, 2007

(65) Prior Publication Data

US 2008/0246960 A1    Oct. 9, 2008

(51) Int. Cl.
*G01N 15/02* (2006.01)
(52) U.S. Cl. .................................................... 356/335
(58) Field of Classification Search .................. None
See application file for complete search history.

(56) References Cited

U.S. PATENT DOCUMENTS 4,220,499 A    9/1980    Hughes, Jr. et al. ........... 162/49
5,293,219 A    3/1994    Ayer .......................... 356/383
5,786,894 A *  7/1998    Shields et al. ............... 356/338

* cited by examiner

*Primary Examiner*—Tu T Nguyen
(74) *Attorney, Agent, or Firm*—Donald J. Ersler

(57) ABSTRACT

A fiber quality transducer includes an inlet mixing probe, a rotating valve sleeve, a camera and a sampling cell. Slurry from a pulp tube flow enters a mixing chamber in the inlet mixing probe. The amount of slurry entering the mixing chamber is controlled by the rotating valve sleeve. The sampling cell includes a first sampling lens and a second sampling lens retained in a sampling bore. The first and second sampling lens are spaced apart to form a sampling space to facilitate the flow of diluted slurry. The camera is retained behind the first sampling lens and a LED back light is retained behind the second sampling lens. The diluted slurry flows past the sampling space. The camera photographs the fibers in the diluted slurry flow. The images from the camera are sent to analyzing software, which determine the characteristics of the fibers in the diluted slurry.

20 Claims, 6 Drawing Sheets

FIBER QUALITY TRANSDUCER

BACKGROUND OF THE INVENTION

1. Field of the Invention

The present invention relates generally to analyzing the characteristics of fibers and more specifically to a fiber quality transducer, which measures the quality of fibers in a stream.

2. Discussion of the Prior Art

Today, a majority of the fiber analyzers available on the market are based on a batch mode sampling system. Typically, pulp is extracted from the production line by means of a piston plunger that extracts a small sample, which is forced into a analyzer unit by means of hydro pressure behind the sample in the sampling tube. Once in the analyzer, the sample is diluted in a sampling tank and a very dilute sample is pumped through a separate loop in front of a measuring device such as a digital camera.

Batch mode sampling requires many components, such as control valves, pumps, frequency drives, level controllers, flow controllers etc., and as a consequence the analyzer units require significant maintenance in order to operate properly. Thus, the cost of installing and operating the analyzer units is very high. A second disadvantage to batch measurements is the sampling frequency. The sampling frequency is typically a low 10-60 min between samples, which limits the use of the analyzer unit to the control of long term variations, namely on an hour basis.

U.S. Pat. No. 4,220,499 to Hughes, Jr. et al. discloses a method for determining the relative quantity of shives in a stream of fibrous particles. The Hughes, Jr. et al. patent includes the continuous sampling and measuring of a production flow line of paper pulp by means of a continuous flow, fiber induction device located within the production line to extract a diluted sample of fiber flow therein. The diluted sample is directed through a windowed conduit section for photodetection of particles therein. However, the Hughes, Jr. et al. patent does not disclose sampling and measuring fibers.

U.S. Pat. No. 5,293,219 to Ayer discloses a fiber length analyzer for batch mode sampling of fibers. The Ayer patent includes a measuring cell in a fiber sample analysis system containing a housing member, which removably supports a transparent flow tube and an optical device, which projects a beam across the tube for detecting and measuring individual fibers in a dilute sample fluid which flows through tube at a constant velocity. The tube includes a gradually narrowing transition portion leading to a measurement portion situated at the optical device.

Accordingly, there is a clearly felt need in the art for a fiber quality transducer, which continuously measures the quality of fibers in a slurry stream in less than one minute for short or long term variations analysis; and greatly reduces the cost of installation and operation, because the reduced number of components allows quantities of particles, such as shives or ray cells to be more accurately accounted for over a longer period of time, due to the ability to analyze millions of particles instead of just thousands.

SUMMARY OF THE INVENTION

The present invention provides a fiber quality transducer, which measures the quality of fibers in a pulp stream. The fiber quality transducer includes an inlet mixing probe, a rotating valve sleeve, a camera and a sampling cell. The inlet mixing probe includes a slurry cross hole, a mixing chamber, at least one water supply passage. The mixing chamber is formed through the length of the inlet mixing probe. The slurry cross hole is formed through substantially a first end of the inlet mixing probe and communicates with a first end of the mixing chamber. A source of water is provided in front of the slurry cross hole to pre-dilute an incoming slurry flow. The amount of pre-diluted slurry entering the mixing chamber is controlled by the rotating valve sleeve. One end of the at least one water supply passage is connected to the mixing chamber and the other end is connected to a supply of water. The slurry is further diluted by a supply of water entering from the at least one water supply passage.

The rotating valve sleeve includes an inner perimeter and a geared flange formed on one end thereof. A slurry inlet is formed through the other end of the rotating valve sleeve. The slurry inlet may be adjusted to be concentric with the slurry cross hole. The inner perimeter of the rotating valve sleeve is sized to rotatably receive an outer perimeter of the inlet mixing probe. A stepper motor with a drive gear is retained adjacent the rotating valve sleeve. The drive gear is engaged with the geared flange of the rotating valve sleeve. Rotation of the rotating valve sleeve controls the amount of slurry entering the slurry cross hole.

The sampling cell includes a first sampling lens and a second sampling lens. The first and second sampling lens are retained in a sampling bore. The first and second sampling lens are spaced apart to form a sampling space to facilitate the flow of diluted slurry. One end of a sampling passage communicates with a second end of the mixing chamber and the other end of the sampling passage communicates with the sampling space. The camera is retained behind the first sampling lens and a LED back light is retained behind the second sampling lens. The diluted slurry flows through the sampling space. The camera photographs the fibers in the diluted slurry flow. The images from the camera are sent to analyzing software, which determine the characteristics of the fibers in the diluted slurry. The diluted slurry is routed back to the pulp tube.

Accordingly, it is an object of the present invention to provide a fiber quality transducer, which continuously measures the quality of fibers in a pulp stream in less than one minute for short or long term variations analysis.

Finally, it is another object of the present invention to provide a fiber quality transducer, which greatly reduces the cost of installation and operation, because the reduced number of components allows quantities of particles, such as shives or ray cells to be more accurately accounted for over a longer period of time.

These and additional objects, advantages, features and benefits of the present invention will become apparent from the following specification.

DETAILED DESCRIPTION OF THE PREFERRED EMBODIMENTS

Figure 1:
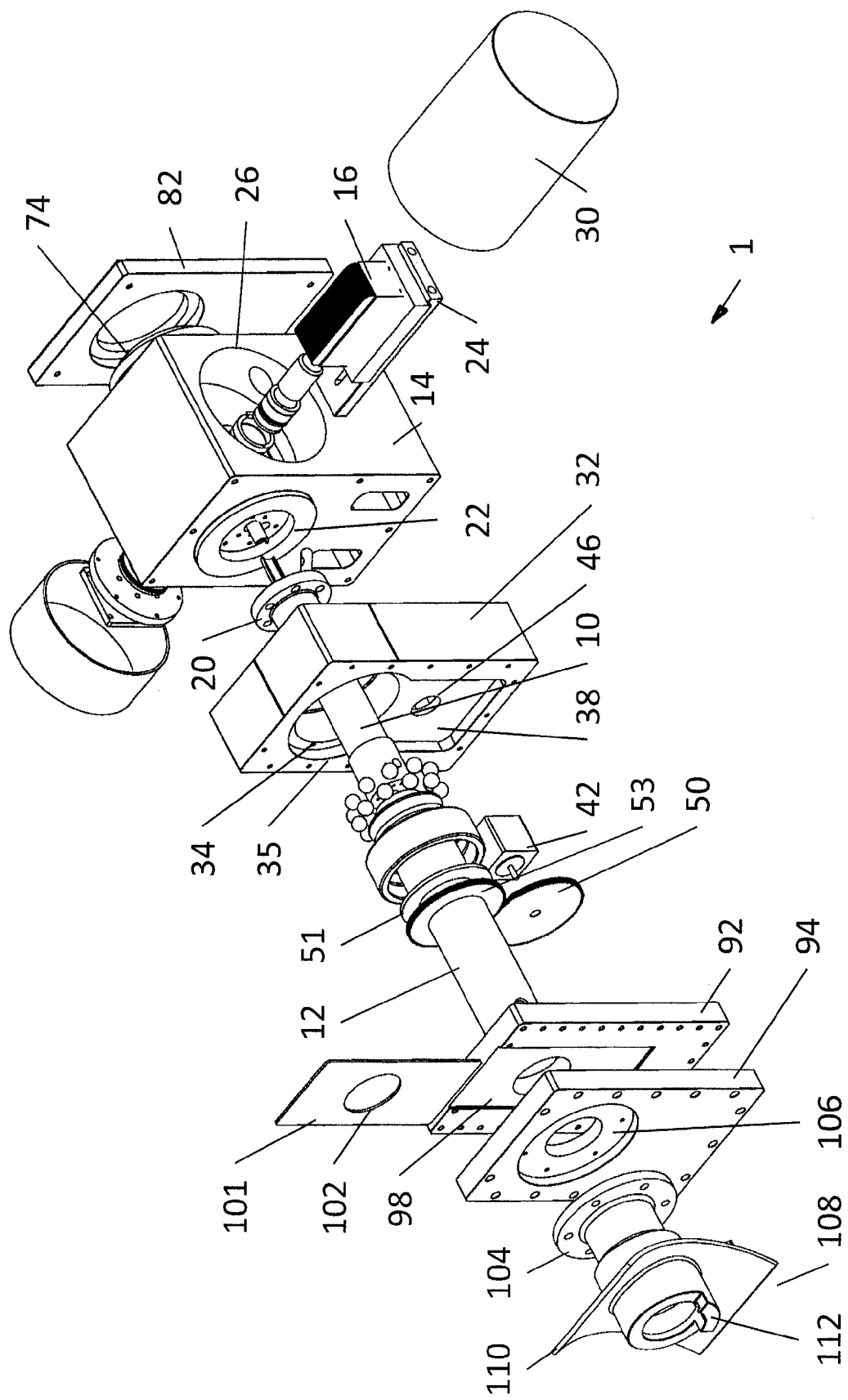
FIG. 1 is a front exploded perspective view of a fiber quality transducer in accordance with the present invention.
Figure 2:
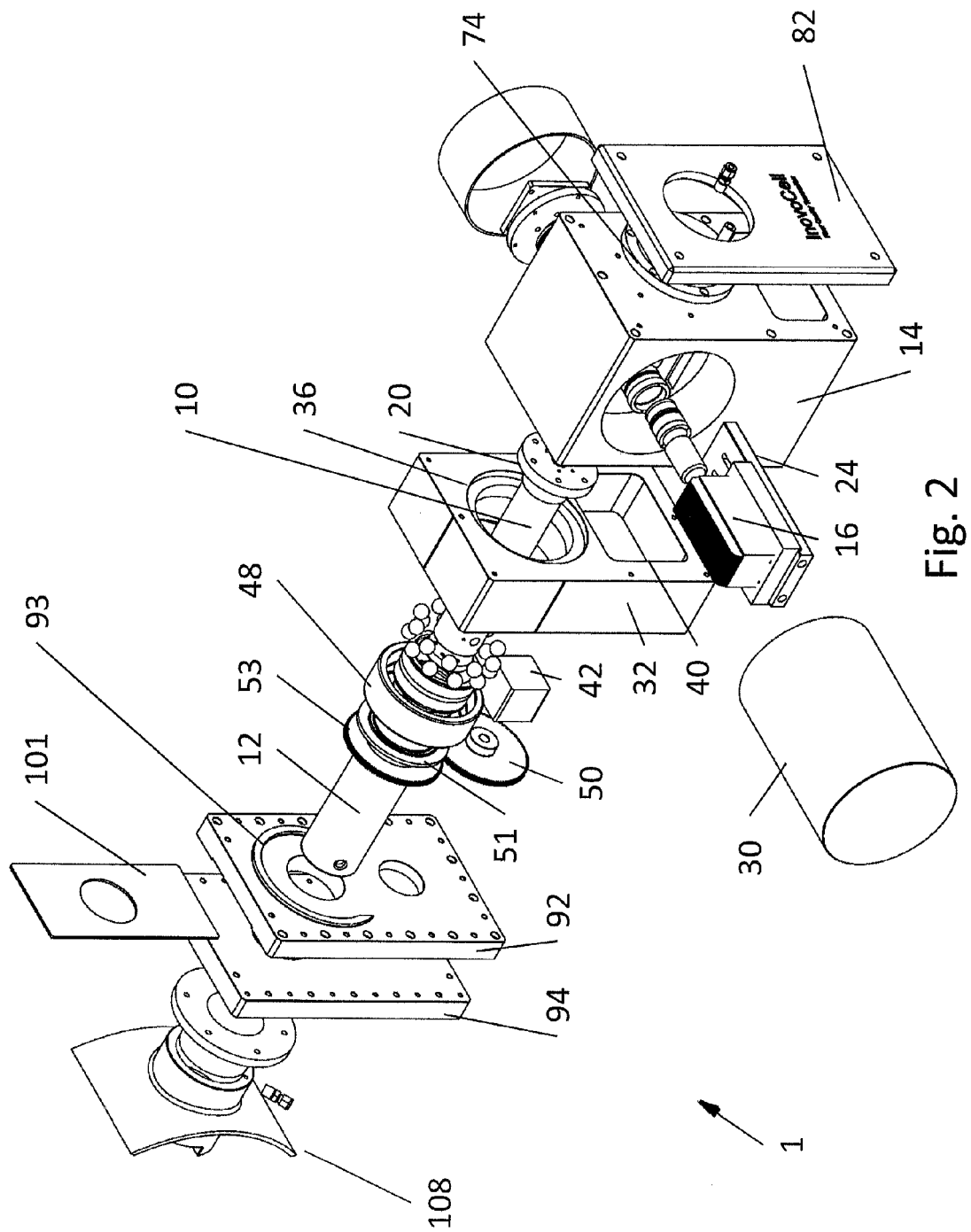
FIG. 2 is a rear exploded perspective view of a fiber quality transducer in accordance with the present invention.
Figure 3:
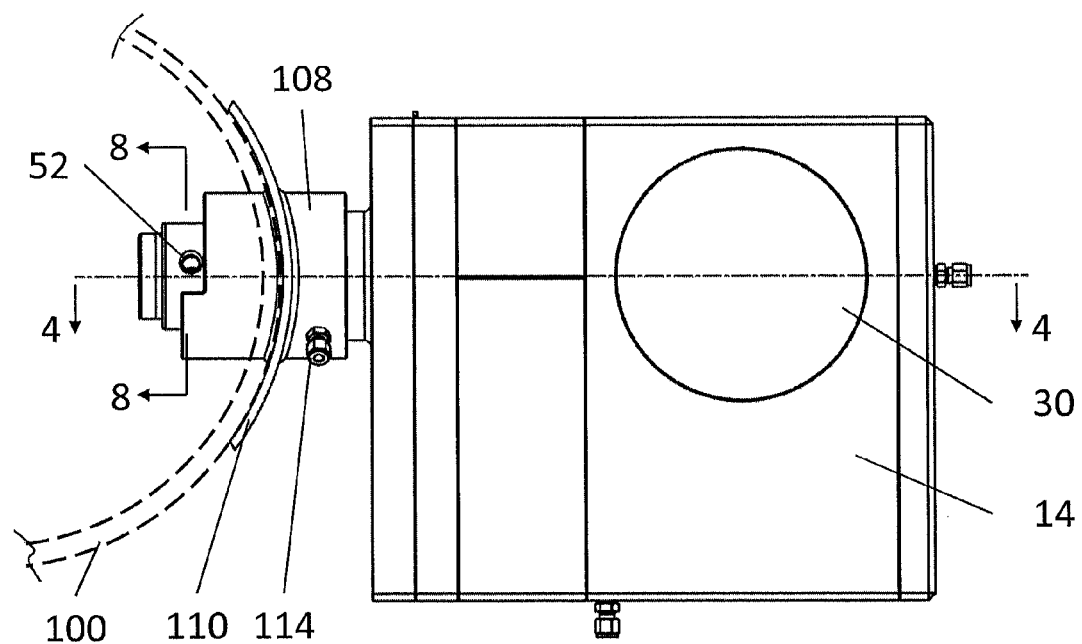
FIG. 3 is a side view of a fiber quality transducer in accordance with the present invention.
Figure 4:
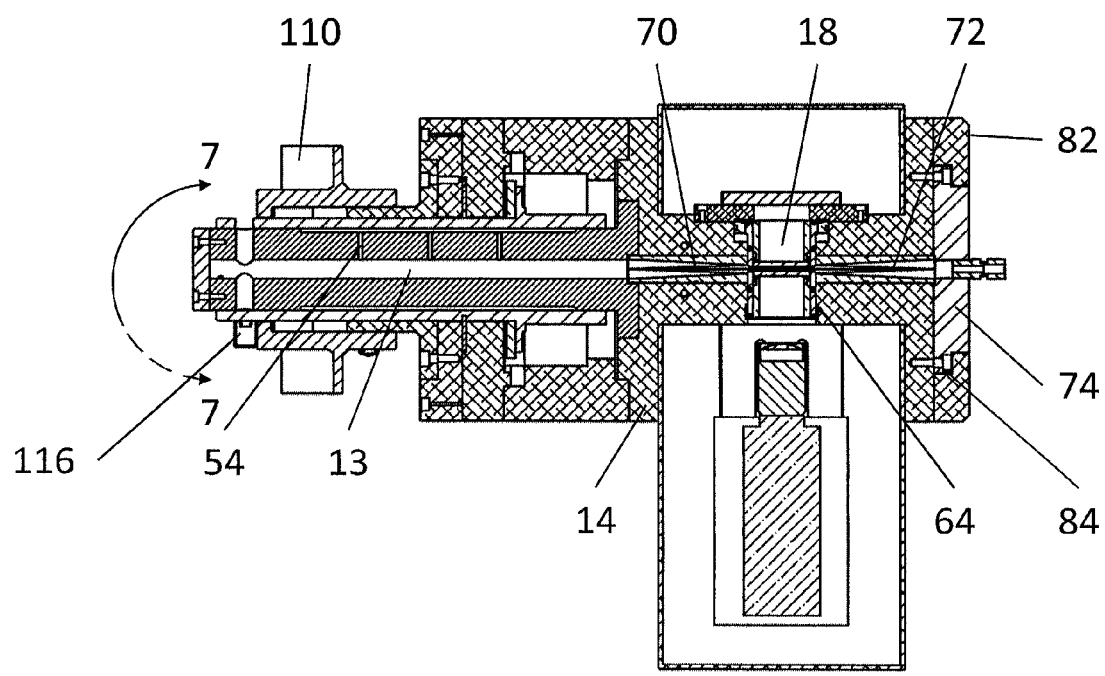
FIG. 4 is a cross sectional view cut through FIG. 3 of a fiber quality transducer in accordance with the present invention.
Figure 7:
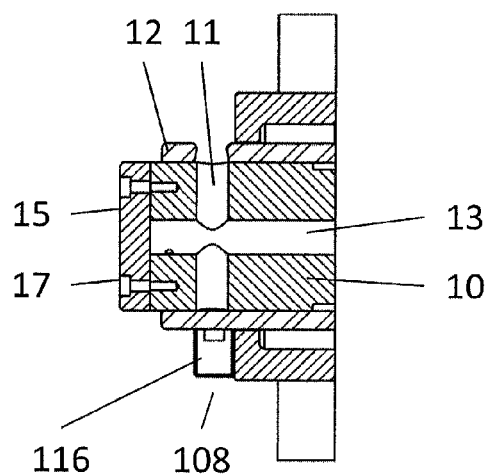
FIG. 7 is an enlarged cross sectional view of a portion of FIG. 4 of a fiber quality transducer in accordance with the present invention.
Figure 8:
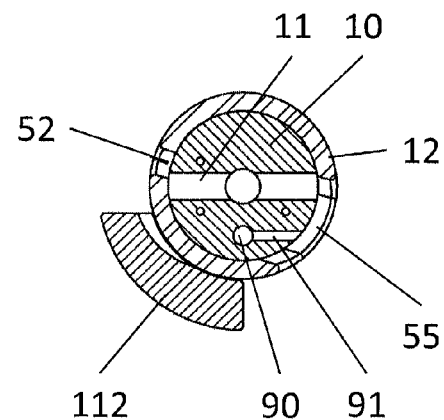
FIG. 8 is a cross sectional view cut through FIG. 3 of a fiber quality transducer in accordance with the present invention.

With reference now to the drawings, and particularly to FIG. 1, there is shown an exploded perspective view of a fiber quality transducer 1. With reference to FIGS. 2-4, the fiber quality transducer 1 includes an inlet mixing probe 10, a rotating valve sleeve 12, a base block 14, a camera 16 and a sampling cell 18. With reference to FIGS. 7-8, the inlet mixing probe 10 includes a slurry cross hole 11 and a mixing chamber 13. The mixing chamber 13 is formed through the length of the inlet mixing probe 10. A closure cap 15 is attached to one end of the inlet mixing probe 10 with at least two fasteners 17 to seal the one end of the mixing chamber 13. The slurry cross hole 11 is formed through substantially the one end of the probe and communicates with one end of the mixing chamber 13. Slurry from a pulp tube 100 enters the slurry cross hole 11. A fastening flange 20 extends radially outward from a second end of the inlet mixing probe 10. A flange bore 22 is located in a first end of the base block 14. The flange bore 22 is sized to firmly receive an outer perimeter of the fastening flange 20. A plurality of fasteners (not shown) are used to secure the fastening flange to a bottom of the flange bore 22.

Figure 6:
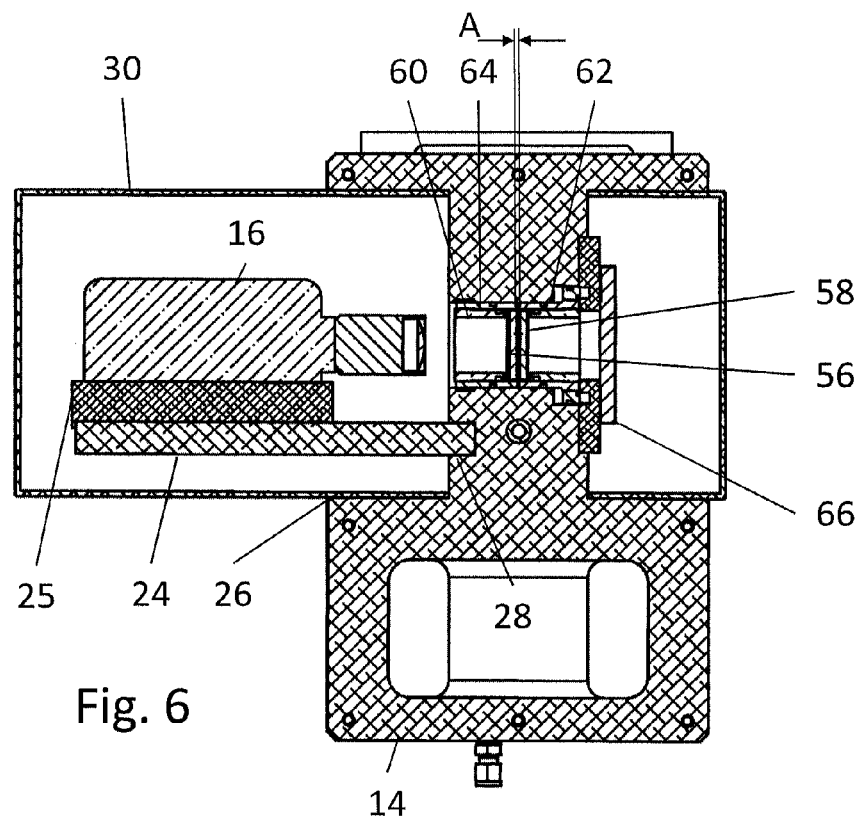
FIG. 6 is an end cross sectional view of a fiber quality transducer in accordance with the present invention.

With reference to FIG. 6, the camera 16 is attached to a retention plate 24. A spacer plate 25 is preferably inserted between the camera 16 and the retention plate 24. The camera 16 is preferably a digital camera providing 10-100 frames per second and having a resolution of between 1.0-12.0 megapixels. However, other cameras having different specifications may also be used. The frame rate depends on the camera resolution. A smaller resolution requires an increased frame rate. A camera bore 26 is formed in a first side of the base block 14.

A plate slot 28 is formed at a bottom of the camera bore 26 to firmly receive an end of the retention plate 24. A plurality of fasteners (not shown) are used to secure the retention plate 24 in the plate slot 28. The camera bore 26 is sized to firmly receive a camera cover 30. The camera cover 30 protects the camera 16 from damage.

A motor retention plate 32 includes a bearing bore 34, a valve housing bore 35, a plate locator bore 36, a gear cavity 38 and a motor cavity 40. The bearing bore 34, valve housing bore 35 and the gear cavity 38 are formed in one side of the motor retention plate 32. The locator bore 36 and motor cavity 40 are formed in the other side of the motor retention plate 32.

Figure 5:
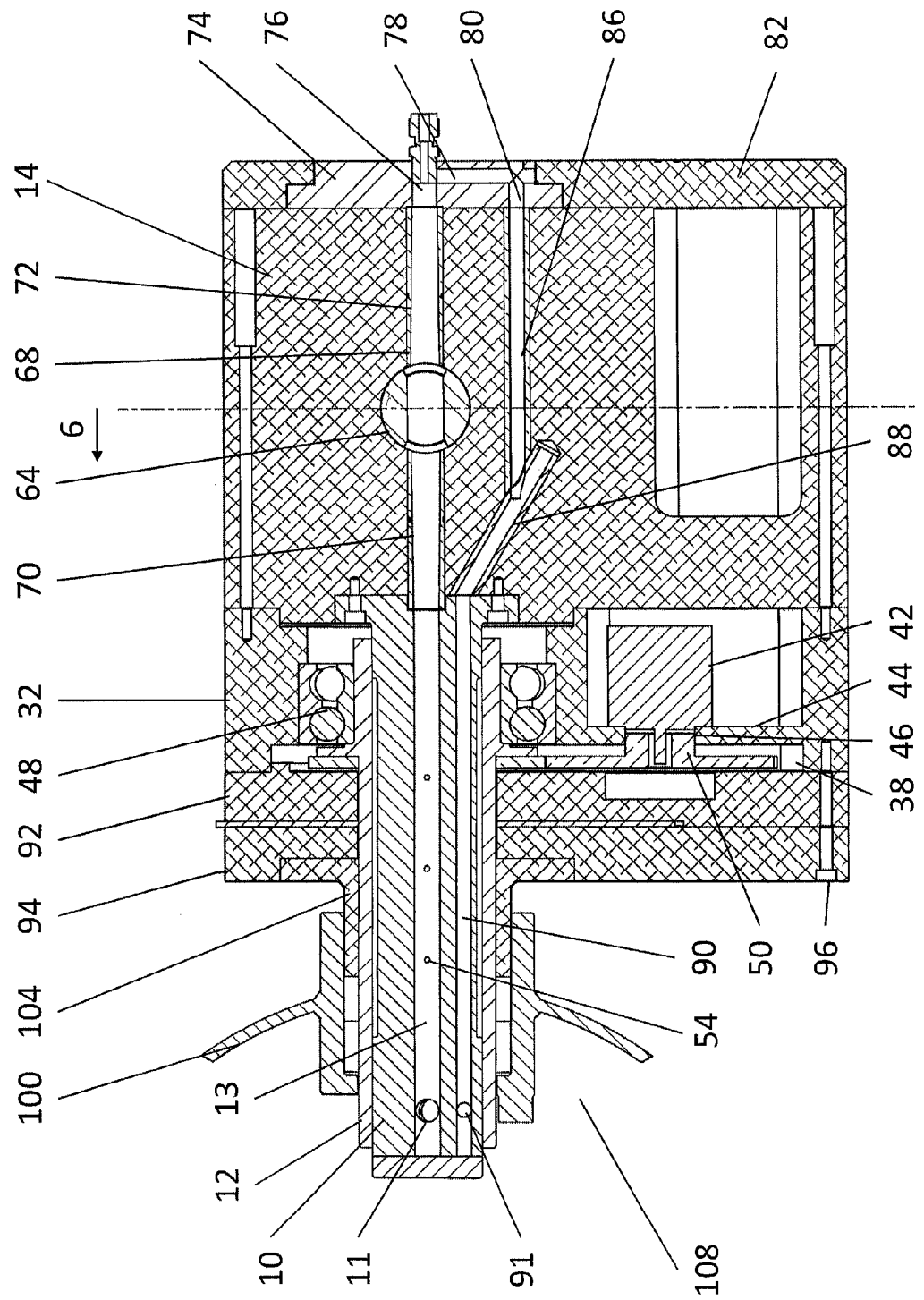
FIG. 5 is a side cross sectional view of a fiber quality transducer in accordance with the present invention.

With reference to FIG. 5, a stepper motor 42 is attached to a mounting web 44 created between the gear cavity 38 and motor cavity 40 with a plurality of fasteners (not shown). A motor locator bore 46 is formed through the mounting web 44 to capture a locating ring of the stepper motor 42. A bearing race 48 is pressed into the bearing bore 34. An inner perimeter of the bearing race 48 of the bearing bore 34 is sized to receive an outer perimeter of the inlet mixing probe 10. A drive gear 50 is attached to a drive shaft of the stepper motor 42.

The rotating valve sleeve 12 includes an inner perimeter and a gear flange 51. The gear flange 51 extends radially outward from one end of the rotating valve sleeve 12. A sleeve gear 53 is secured to the gear flange 51 with any suitable method. The inner perimeter of the rotating valve sleeve 12 is sized to rotatably receive an outer perimeter of the inlet mixing probe 10. The sleeve gear 53 engages the drive gear 50. The stepper motor 42 rotates the rotating valve sleeve 12 to control the amount of slurry entering through a slurry inlet 52 and the slurry cross hole 11 and exiting through a slot opening 55 in the rotating sleeve 12. The rotating valve sleeve 12 enables the inlet and outlet of the cross hole 11 to be closed, depending on its clockwise or counterclockwise rotation. The slurry inlet 52 may be adjusted to be concentric with the slurry cross hole 11 of the inlet mixing probe 10.

The inlet mixing probe 10 further includes at least one water supply passage 54 in communication with the mixing chamber 13. The other end of the at least one water supply passage 54 is connected to a supply of water. The slurry is diluted by a supply of water entering from the at least one water supply passage 54. The sampling cell 18 includes a first sampling lens 56 and a second sampling lens 58. The first sampling lens 56 is preferably retained in a first lens housing 60. The second sampling lens 58 is preferably retained in a second lens housing 62. The first and second lens housings are both retained in a lens bore 64. However, other methods of retaining the first and second sampling lens 56 may also be used.

Figure 9:
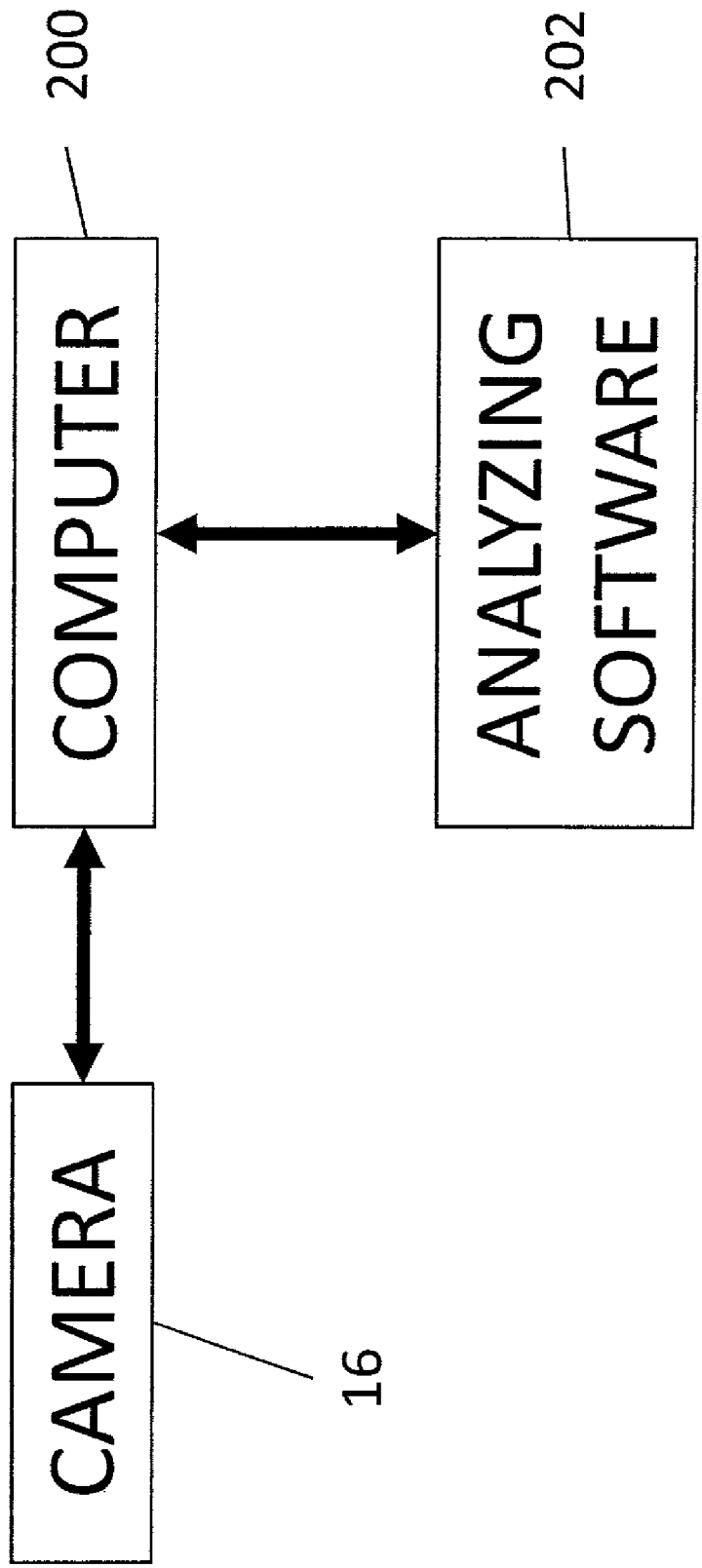
FIG. 9 is a block diagram of a camera connected to a computer of a fiber quality transducer in accordance with the present invention.

A sampling space is created between the first and second sampling lens 58 and defined by gap "A." The camera 16 photographs the fibers in the diluted slurry that flow through the sampling space. An LED back light 66 is mounted behind the second sampling lens 58 to provide illumination of the diluted slurry for the camera 16. With reference to FIG. 9, the images from the camera 16 are sent to a computer 200 that includes fiber analyzing software 202. The fiber analyzing software 202 determines the characteristics of the fibers in the diluted slurry. Fiber analyzing software is well known in the art and need not be explained in detail.

A sampling bore 68 is formed through the base block 14 on the same axis as the lens bore 64. A first sampling tube 70 is inserted into the sampling bore 68 on one side of the lens bore 64 and a second sampling tube 72 is inserted into the sampling bore 68 on the other side of the lens bore 64. One end of the first sampling tube 70 communicates with the second end of the mixing chamber 13. An inner perimeter of the first sampling tube 70 tapers inward to form a smaller opening on a second end than on a first end. A first end of the second sampling tube 72 adjacent the lens bore tapers outward to form a larger opening on a second end than on a first end.

Diluted slurry flowing through the second end of the second sampling tube 72 is diverted by a diverter plate 74. The diverter plate 74 includes a forward passage 76, a vertical passage 78 and a return passage 80. The forward passage 76 communicates with the second end of the second sampling tube 72. One end of the vertical passage 78 communicates with the forward passage 76 and the other end communicates with the return passage 80. The diverter plate 74 is retained against the second end of the base block 14 with a diverter retention plate 82. The diverter retention plate 82 is attached to the base block 14 with at least two fasteners 84.

A first return tube 86 is pressed into the second end of the base block 14 and a second return tube 88 is pressed into the first end of the base block 14, such that the first and second return tubes communicate with each other. The first and second return tubes are fabricated from a noncorrosive material. A diluted slurry return passage 90 is formed through the length of the inlet mixing probe 10, adjacent the mixing chamber 13. Diluted slurry passes through the first return tube 86, the second return tube 88 and the diluted slurry return passage 90 and exits through an output passage 91.

An inner valve housing 92 and an outer valve housing 94 are attached to the motor retention plate 32 with a plurality of fasteners 96. A valve slot 98 is formed in a first side of the inner valve housing 92 to slidably retain a plate valve 101. The plate valve 101 includes a sleeve clearance hole 102 to receive the rotating valve sleeve 12. A locating projection 93 is formed on a second side of the inner valve housing 92. The locating projection 93 is sized to be received by the valve housing bore 35. A manifold ring 104 is retained in a ring bore 106 formed in a first side of the outer valve housing 94. The manifold ring 104 is secured to the outer valve housing 94 with a plurality of fasteners (not shown). The manifold ring 104 includes an inner perimeter that is sized to receive the rotating valve sleeve 12.

An interfacing manifold 108 includes a tube flange 110 and a diverter projection 112. An inner perimeter of the interfacing manifold 108 is sized to receive an end of the manifold ring 104. With reference to FIGS. 3, 4 and 7, pressurized water enters nipple 114 and passes through the interfacing manifold 108 to a diluting output 116. The pressurized water streaming from the diluting output 116 dilutes the slurry entering the slurry cross hole 11. Normally, the slurry would be too thick to enter the slurry cross hole 11 without pre-dilution from the diluting output 116. Once the diluted slurry enters the mixing chamber 13, the diluted slurry is further diluted by water entering the mixing chamber 13 through the at least one water supply passage 54.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. A method of continuously analyzing the characteristics of fibers in a slurry flow, comprising the steps of:
   supplying continuously slurry flow into a mixing chamber from a pulp tube;
   diluting continuously the slurry flow in said mixing chamber with water to form a diluted slurry flow without stopping the slurry flow or the diluted slurry flow;
   streaming continuously said diluted slurry flow through a sampling space, photographing fibers in the diluted slurry flow continuously passing through said sampling space; and
   determining the characteristics of the photographed fibers in the diluted slurry flow.

2. The method of continuously analyzing the characteristics of fibers in a slurry flow of claim 1, further comprising the step of:
   routing the diluted slurry flow back to the pulp tube.

3. The method of continuously analyzing the characteristics of fibers in a slurry flow of claim 1, further comprising the step of:
   diluting the slurry flow with water before entry into said mixing chamber.

4. The method of continuously analyzing the characteristics of fibers in a slurry flow of claim 1, further comprising the step of:
   providing a computer having fiber analyzing software to determine the characteristics of the photographed fibers.

5. The method of continuously analyzing the characteristics of fibers in a slurry flow of claim 1, further comprising the step of:
   creating said sampling space by locating a gap between a first lens and a second lens, locating a camera behind said first lens, locating a LED back light behind said second lens.

6. The method of continuously analyzing the characteristics of fibers in a slurry flow of claim 1, further comprising the step of:
   forming said mixing chamber in an inlet mixing probe, inserting said inlet mixing probe into a rotating valve sleeve, rotation of said rotating valve sleeve controlling the amount of slurry flow entering said mixing chamber.

7. The method of continuously analyzing the characteristics of fibers in a slurry flow of claim 6, further comprising the step of:
   providing an interfacing manifold having pressurized water streaming from a diluting output, retaining said interfacing manifold on said rotating valve sleeve, attaching said interfacing manifold to the pulp tube.

8. A method of continuously analyzing the characteristics of fibers in a slurry flow, comprising the steps of:
   supplying continuously slurry flow into a mixing chamber from a pulp tube;
   diluting continuously the slurry flow in said mixing chamber with water to form a diluted slurry flow without stopping the slurry flow or the diluted slurry flow;
   streaming continuously the diluted slurry flow through a sampling space, photographing fibers in the diluted slurry flow continuously passing through said sampling space;
   determining the characteristics of the photographed fibers in the diluted slurry flow; and
   routing the diluted slurry flow back to the pulp tube.

9. The method of continuously analyzing the characteristics of fibers in a slurry flow of claim 8, further comprising the step of:
   diluting the slurry flow with water before entry into said mixing chamber.

10. The method of continuously analyzing the characteristics of fibers in a slurry flow of claim 8, further comprising the step of:
    providing a computer having fiber analyzing software to determine the characteristics of the photographed fibers.

11. The method of continuously analyzing the characteristics of fibers in a slurry flow of claim 8, further comprising the step of:
    creating said sampling space by locating a gap between a first lens and a second lens, locating a camera behind said first lens, locating a LED back light behind said second lens.

12. The method of continuously analyzing the characteristics of fibers in a slurry flow of claim 8, further comprising the step of:
    forming said mixing chamber in an inlet mixing probe, inserting said inlet mixing probe into a rotating valve sleeve, rotation of said rotating valve sleeve controlling the amount of slurry flow entering said mixing chamber.

13. The method of continuously analyzing the characteristics of fibers in a slurry flow of claim 12, further comprising the step of:
    providing an interfacing manifold having pressurized water streaming from a diluting output, retaining said interfacing manifold on said rotating valve sleeve, attaching said interfacing manifold to the pulp tube.

14. A method of continuously analyzing the characteristics of fibers in a slurry flow, comprising the steps of:
    supplying continuously slurry flow into a mixing chamber from a pulp tube;

diluting continuously the slurry flow in said mixing chamber with water to form a diluted slurry flow without stopping the slurry flow or the diluted slurry flow;

streaming continuously said diluted slurry flow through a sampling space, photographing fibers in the diluted slurry flow continuously passing through said sampling space; and determining the characteristics of the photographed fibers in the diluted slurry flow with fiber analyzing software.

15. The method of continuously analyzing the characteristics of fibers in a slurry flow of claim 14, further comprising the step of:

routing the diluted slurry flow back to the pulp tube.

16. The method of continuously analyzing the characteristics of fibers in a slurry flow of claim 14, further comprising the step of:

diluting the slurry flow with water before entry into said mixing chamber.

17. The method of continuously analyzing the characteristics of fibers in a slurry flow of claim 14, further comprising the step of:

providing a computer having said fiber analyzing software to determine the characteristics of the photographed fibers.

18. The method of continuously analyzing the characteristics of fibers in a slurry flow of claim 14, further comprising the step of:

creating said sampling space by locating a gap between a first lens and a second lens, locating said photographic device behind said first lens, locating a LED back light behind said second lens.

19. The method of continuously analyzing the characteristics of fibers in a slurry flow of claim 18, further comprising the step of:

providing an interfacing manifold having pressurized water streaming from a diluting output, retaining said interfacing manifold on said rotating valve sleeve, attaching said interfacing manifold to the pulp tube.

20. The method of continuously analyzing the characteristics of fibers in a slurry flow of claim 14, further comprising the step of:

forming said mixing chamber in an inlet mixing probe, inserting said inlet mixing probe into a rotating valve sleeve, rotation of said rotating valve sleeve controlling the amount of slurry flow entering said mixing chamber.

* * * * *